(12) United States Patent
Zuckerman et al.

(10) Patent No.: US 8,581,579 B2
(45) Date of Patent: Nov. 12, 2013

(54) MAGNETO ELECTRIC SENSOR WITH INJECTED UP-CONVERSION OR DOWN-CONVERSION

(75) Inventors: Lawrence H. Zuckerman, Livermore, CA (US); Michael X. Maida, Sunnyvale, CA (US); Dennis M. Monticelli, Fremont, CA (US); James B. Wieser, Livermore, CA (US); Jamal Ramdani, Scarborough, ME (US)

(73) Assignee: National Semiconductor Corporation, Santa Clara, CA (US)

(*) Notice: Subject to any disclaimer, the term of this patent is extended or adjusted under 35 U.S.C. 154(b) by 490 days.

(21) Appl. No.: 12/927,205

(22) Filed: Nov. 9, 2010

(65) Prior Publication Data

US 2011/0148403 A1    Jun. 23, 2011

Related U.S. Application Data

(60) Provisional application No. 61/280,808, filed on Nov. 9, 2009, provisional application No. 61/332,592, filed on May 7, 2010, provisional application No. 61/356,403, filed on Jun. 18, 2010.

(51) Int. Cl.
    *G01R 33/12* (2006.01)
(52) U.S. Cl.
    USPC .......................................... 324/239; 324/228
(58) Field of Classification Search
    None
    See application file for complete search history.

(56) References Cited

U.S. PATENT DOCUMENTS

| 4,673,827 | A | 6/1987 | Sommer |
| 5,767,668 | A | 6/1998 | Durand |
| 2001/0028245 | A1 | 10/2001 | Li et al. |
| 2001/0040450 | A1 | 11/2001 | Li et al. |
| 2004/0126620 | A1* | 7/2004 | Viehland et al. ............. 428/692 |
| 2009/0230953 | A1* | 9/2009 | Lee ............................. 324/244 |

FOREIGN PATENT DOCUMENTS

JP            2001028466 A        1/2001

OTHER PUBLICATIONS

Notification of Transmittal of the International Search Report and the Written Opinion of the International Searching Authority, or the Declaration dated Jun. 30, 2011 in connection with International Patent Application No. PCT/US2010/056047.
Notification of Transmittal of the International Search Report and the Written Opinion of the International Searching Authority, or the Declaration dated Jun. 30, 2011 in connection with International Patent Application No. PCT/US2010/056054.

* cited by examiner

*Primary Examiner* — Jermele M Hollington
*Assistant Examiner* — Trung Nguyen
(74) *Attorney, Agent, or Firm* — Andrew Viger; Wade J. Brady, III; Frederick J. Telecky, Jr.

(57) ABSTRACT

A method includes generating an electrical signal representing a magnetic field using a magnetic field sensor having alternating layers of magneto-strictive material and piezo-electric material. The method also includes performing up-conversion or down-conversion so that the electrical signal representing the magnetic field has a higher or lower frequency than a frequency of the magnetic field. The up-conversion or down-conversion is performed before the magnetic field is converted into the electrical signal. The up-conversion or down-conversion could be performed by repeatedly sensitizing and desensitizing the magnetic field sensor. This could be done using a permanent magnet and an electromagnet, an electromagnet without a permanent magnet, or a movable permanent magnet. The up-conversion or down-conversion could also be performed by chopping the magnetic field. The chopping could involve intermittently shielding the magnetic field sensor from the magnetic field or moving the magnetic field sensor with respect to the magnetic field.

15 Claims, 4 Drawing Sheets

MAGNETO ELECTRIC SENSOR WITH INJECTED UP-CONVERSION OR DOWN-CONVERSION

CROSS-REFERENCE TO RELATED APPLICATIONS AND PRIORITY CLAIM

This application claims priority under 35 U.S.C. §119(e) to the following U.S. provisional patent applications:
U.S. Provisional Patent Application No. 61/280,808 filed on Nov. 9, 2009;
U.S. Provisional Patent Application No. 61/332,592 filed on May 7, 2010; and
U.S. Provisional Patent Application No. 61/356,403 filed on Jun. 18, 2010.
All three of these patent applications are hereby incorporated by reference.

TECHNICAL FIELD

This disclosure relates generally to magnetic field sensors. More specifically, this disclosure relates to a magneto-electric sensor with injected up-conversion or down-conversion.

BACKGROUND

It is often necessary or desirable to measure extremely weak magnetic fields. For example, it has been shown that magnetic fields generated by currents in a person's heart can be used to identify possible heart disease. However, these magnetic fields are extremely weak, often about 20 picotesla or "pT" peak-to-peak. It is typically very difficult to measure these types of weak or even weaker magnetic fields without highly specialized and expensive equipment.

BRIEF DESCRIPTION OF DRAWINGS

For a more complete understanding of this disclosure and its features, reference is now made to the following description, taken in conjunction with the accompanying drawings, in which.

DETAILED DESCRIPTION

FIGS. 1 through 7, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1:
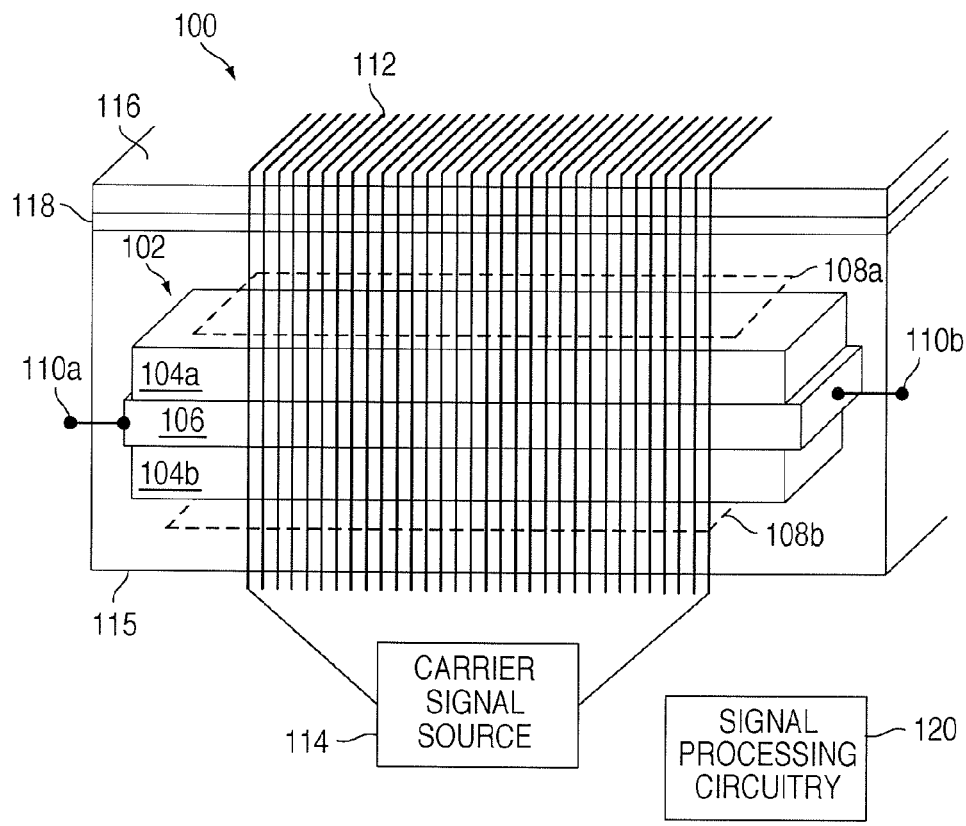
FIG. 1 illustrates an example magneto-electric sensor with injected up-conversion or down-conversion according to this disclosure.

FIG. 1 illustrates an example magneto-electric sensor 100 with injected up-conversion or down-conversion according to this disclosure. As shown in FIG. 1, the sensor 100 includes a sensor stack 102 having alternating magneto-strictive and piezo-electric layers. In this example, layers 104a-104b are magneto-strictive, and layer 106 is piezo-electric. The magneto-strictive layers 104a-104b lengthen and shorten depending on an ambient magnetic flux density value. As the magneto-strictive layers 104a-104b are physically attached (such as laminated) to the piezo-electric layer 106, the piezo-electric layer 106 also lengthens and shortens. The piezo-electric effect results in a charged capacitance whose voltage is an analog version of surrounding magnetic field measurements.

While two magneto-strictive layers 104a-104b and one piezo-electric layer 106 are shown in FIG. 1, the sensor 100 could include any number of magneto-strictive and piezo-electric layers. The sensor 100 could, for example, include tens or hundreds of magneto-strictive and piezo-electric layers. Additional details regarding the use of magneto-strictive and piezo-electric materials to measure magnetic fields can be found in "Detection of pico-Tesla magnetic fields using magneto-electric sensors at room temperature," Appl. Phys. Lett. 88, 062510 (2006) and U.S. Pat. No. 7,023,206 (both of which are hereby incorporated by reference).

Each magneto-strictive layer 104a-104b could be formed from any suitable magneto-strictive material(s), such as TER-FENOL D or METGLAS. Each piezo-electric layer 106 could be formed from any suitable piezo-electric material(s), such as quartz or PZT (lead zirconate titanate). Each of these layers could also be formed in any suitable manner. For instance, one or more magneto-strictive layers could be formed by sputtering the magneto-strictive material(s) onto a piece of piezo-electric material.

One or more permanent magnets 108a-108b are used in the sensor 100 to immerse the magneto-strictive layers in a biasing magnetic field, such as a substantially constant time-invariant direct current (DC) magnetic field of considerable amplitude. When the biasing magnetic field of a correct value has field lines parallel to the longitudinal direction of the layers 104a-104b, the layers 104a-104b lengthen and shorten in proportion with the instantaneous value of the component of the magnetic field parallel to the longitudinal direction of the layers 104a-104b. As a result, the lengthening and shortening of the magneto-strictive layers 104a-104b (and thus the piezo-electric layer 106) is proportional to the surrounding magnetic field. Each permanent magnet 108a-108b could include any suitable magnetic structure. Note that while two permanent magnets 108a-108b are shown in specific positions in FIG. 1, the sensor 100 could include one or more than two permanent magnets in any suitable location(s).

Electrical connections 110a-110b provide electrical signals from the sensor 100 to external components. For example, the connections 110a-110b could be coupled to signal processing circuitry 120. The connections 110a-110b include any suitable structures providing electrical connectivity to the sensor 100.

A sensor formed only by components 102-110b would act essentially as an AC generator in series with a small value capacitor. The effective capacitance of this sensor varies relatively little, such as from about 700 pF at 3 Hz to about 300 pF at 50 kHz. However, the reactance of this sensor varies widely, and the reactance of this sensor becomes very large at low frequencies. This makes it difficult to transfer an extremely weak signal's power to the signal processing circuitry, which itself often needs an extremely high input impedance. Unlike piezo-electric elements used in electronic circuitry for frequency control and filters, this piezo-electric sensor can display a large change of resistance. For instance, the sensor could have a resistance of several mega-Ohms at a few Hertz, a resistance of about 300 kΩ at 100 Hz, and a resistance of about 1 kΩ at 40 kHz. Such large resistance variation implies a large variation of how signal power can be extracted from the sensor.

In accordance with this disclosure, the sensor 100 can implement up-conversion to obtain a stronger signal from the sensor 100. As noted above, the permanent magnet(s) 108a-108b can generate a biasing magnetic field, which sensitizes the sensor 100 so that the sensor 100 can accurately measure the surrounding magnetic field. The sensor 100 also uses an additional magnetic field to substantially reduce or cancel the biasing magnetic field generated by the permanent magnet(s) 108a-108b at certain times, effectively desensitizing the sensor 100 during those times. This additional magnetic field can be generated using an electromagnet, which in this example is formed using a solenoid 112 coupled to a carrier signal source 114. The carrier signal source 114 generates a drive signal that drives the electromagnet, such as a current that flows through the solenoid 112, to create the additional magnetic field. The drive signal has a frequency that causes the electromagnet to repeatedly turn on and off, which repeatedly sensitizes and desensitizes the sensor 100. The solenoid 112 includes any suitable structure having a suitable number of windings, and the solenoid 112 could be formed from any suitable conductive material(s). The carrier signal source 114 includes any suitable structure for generating a drive signal at a specified frequency.

In one aspect of operation, a signal through the solenoid 112 turns the electromagnet on and off at a specified carrier frequency rate. The carrier frequency can be much higher in frequency than the sensed magnetic field's highest frequency of interest, such as approximately 10 kHz to approximately 50 kHz for a 3 Hz signal of interest. This causes the electromagnet to cyclically turn on to cancel the biasing magnetic field and turn off to restore the biasing magnetic field, which repeatedly desensitizes and sensitizes the sensor 100. For instance, a carrier signal could supply adequate current to cancel the biasing magnetic field of the permanent magnets 108a-108b during half of a carrier cycle and no current (restoring the biasing magnetic field) during the other half of the carrier cycle.

Effectively, this modulates the biasing magnetic field with the carrier signal. The sensor 100 becomes an up-converting heterodyne mixer, and a targeted low frequency signal (such as 3 Hz) leaves the sensor 100 as coherent sidebands near the higher carrier frequency. At these higher sideband frequencies, the reactance of the piezo-capacitance of the sensor 100 is much smaller compared to the piezo-capacitance of the sensor 100 at the lower frequency (such as 12 kΩ versus 100 MΩ), and the series resistance is much smaller. The series reactance of the sensor 100 is low enough that it could be cancelled with a series-resonating inductor, thus leaving only the series resistance of the sensor 100. This permits the sensor 100 to deliver a signal with orders of magnitude more signal power.

In this example, a sensor enclosure 115 encasing other components of the sensor 100 can be split or divided so that its lid 116 or other portion is electrically separated from the remainder of the enclosure 115. This could be done using a dielectric material 118, such as KAPTON polyimide tape. This can help to prevent an unwanted short-circuited secondary turn. The enclosure 115 could be formed from any suitable material(s), such as aluminum. Note that the placement of two permanent magnets 108a-108b inside the enclosure 115 is for illustration only. Any number of permanent magnets could be used within or outside of the enclosure 115, and the magnet(s) could be placed in any suitable position(s). Also note that the windings of the solenoid 112 are placed outside the enclosure 115 in FIG. 1. Again, this is for illustration only. The solenoid's winding could be placed in any other suitable location, such as inside the enclosure 115. In addition, the use of a solenoid winding is for illustration only. Any other structure(s) forming an electromagnet could be used to substantially or completely cancel the biasing magnetic field, such as Helmholz coils.

The sensor 100 can be used in an analog front end (AFE) or other architecture to deliver a signal having an improved signal-to-noise ratio (SNR) compared to conventional magneto-electric sensors. The sensor 100 can make more output power available to AFE or other circuitry, reduce or avoid the need for extremely high input resistances, and/or reduce or avoid 1/f noise present at lower frequency bands of interest (such as around 3 Hz). This is accomplished by converting the lower-frequency signal of interest to a higher-frequency signal within the sensor 100 itself, as opposed to chopping the lower-frequency signal to heterodyne it to a higher frequency outside the sensor 100 after the lower-frequency signal has passed out of the sensor 100 through a very high impedance.

The output of the sensor 100 could be processed in any suitable manner by the signal processing circuitry 120. For example, following a suitable amount of pass-band amplification around the carrier frequency, the signal can be down-converted back to baseband (such as around 3 Hz) using a synchronous detector. Inasmuch as the same carrier signal is used for up-conversion and down-conversion, no locking loop may be needed, and carrier noise (which can be large close to the carrier frequency where the low frequency signal resides) can be cancelled. In general, the signal processing circuitry 120 includes any suitable components for processing the signals from the sensor 100. This processing can be done, for instance, to isolate or use the measurements of the surrounding magnetic field. Various examples of signal processing circuits are shown in the U.S. provisional patent applications incorporated by reference above. The up-conversion functionality described above is useful since, with a much higher front-end frequency, the reactance from the sensor's series capacitance drops by several orders of magnitude, providing a much higher-powered signal to a preamplifier or other signal processing circuitry 120. Also, the signal processing circuitry 120 can have much less noise at higher frequencies than at low frequencies like 3 Hz.

In some embodiments, using a combination of one or more permanent magnets 108a-108b to create the biasing field that sensitizes the sensor 100 and an electromagnet to cancel this field to desensitize the sensor 100 may be superior to using just an electromagnet by itself. This is because the electromagnet with its carrier noise is turned off during the half-cycles when the sensor 100 is active, leaving only the inherently quiet permanent magnet(s). When the electromagnet is (fully) energized, the sensor is inactive, so the electromagnet noise is of no consequence.

Figure 2:
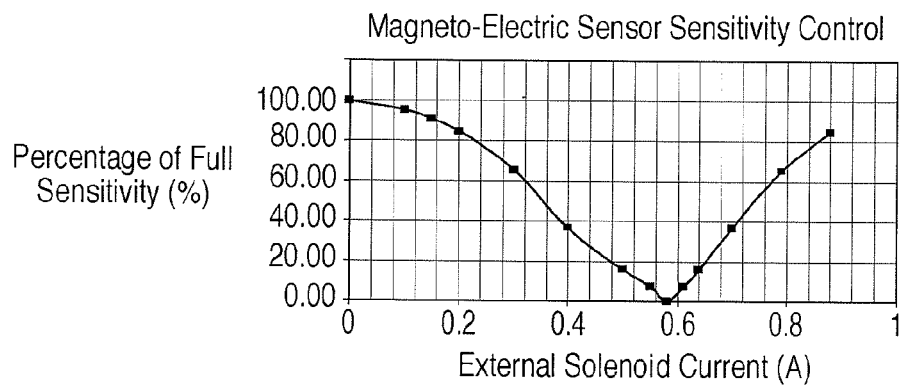
FIG. 2 illustrates an example relationship between sensor sensitivity and electromagnet coil current in a magneto-electric sensor according to this disclosure.

As noted above, the biasing magnetic field from the magnets 108a-108b can be reduced or cancelled using the electromagnet. FIG. 2 illustrates an example relationship between sensor sensitivity and electromagnet coil current in a magneto-electric sensor according to this disclosure. As shown in FIG. 2, the sensor's sensitivity versus electromagnet coil current can be a generally well-behaved function. In this example, as the current through the solenoid 112 increases from 0 A to 0.58 A, the field from the electromagnet gradually cancels out the field from the permanent magnets 108a-108b, reducing the sensor's sensitivity to zero. Then, as the current continues to increase, the net magnetic field restores the sensor's sensitivity.

Note that the sensor's sensitivity versus current and net magnetic field is substantially linear over a wide range. Gain variation being linear with current implies that the transfer characteristic is square law. This indicates that, for example, an approximately 10 kHz to approximately 50 kHz carrier signal operating within this range can make an excellent square law mixer. Also note that the behavior shown in FIG. 2 holds for a specific implementation of the sensor 100. Other implementations of the sensor 100 could have other behaviors. For instance, the behavior of the sensor 100 could vary based on the turn density of the solenoid 112.

FIGS. 3 through 6 illustrate details of an example up-conversion in a magneto-electric sensor according to this disclosure. In particular, FIGS. 3 through 6 illustrate up-conversion details for a specific implementation of the sensor 100. In the specific implementation, the solenoid 112 has an inductance of about 300 μH, and the carrier signal source 114 provides a carrier signal ranging from 0 A to about 0.6 A at a frequency of 20 kHz. Also, the sensor 100 generates a 3.5 mV peak-to-peak signal based on a magnetic field from nearby 60 Hz electrical lines.

Figure 3:
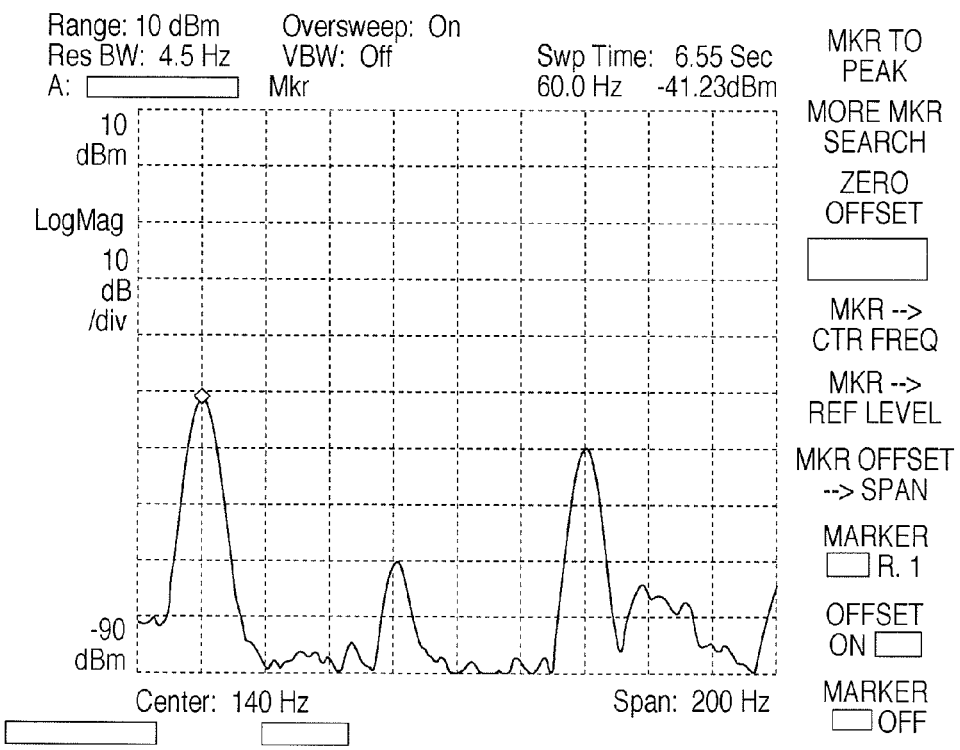
FIGS. 3 through 6 illustrate details of an example up-conversion in a magneto-electric sensor according to this disclosure.

FIG. 3 shows the sensor output when the sensor 100 is connected to a spectrum analyzer with a 1 MΩ input resistance. The analyzer is set to examine the baseband signal, and the carrier signal source 114 is turned off. FIG. 3 therefore shows the output of the sensor 100 without up-conversion. As can be seen here, a 60 Hz component (the left peak) shows at −41 dBm on the scale. Also shown are second, third, and fourth harmonics.

Figure 4:
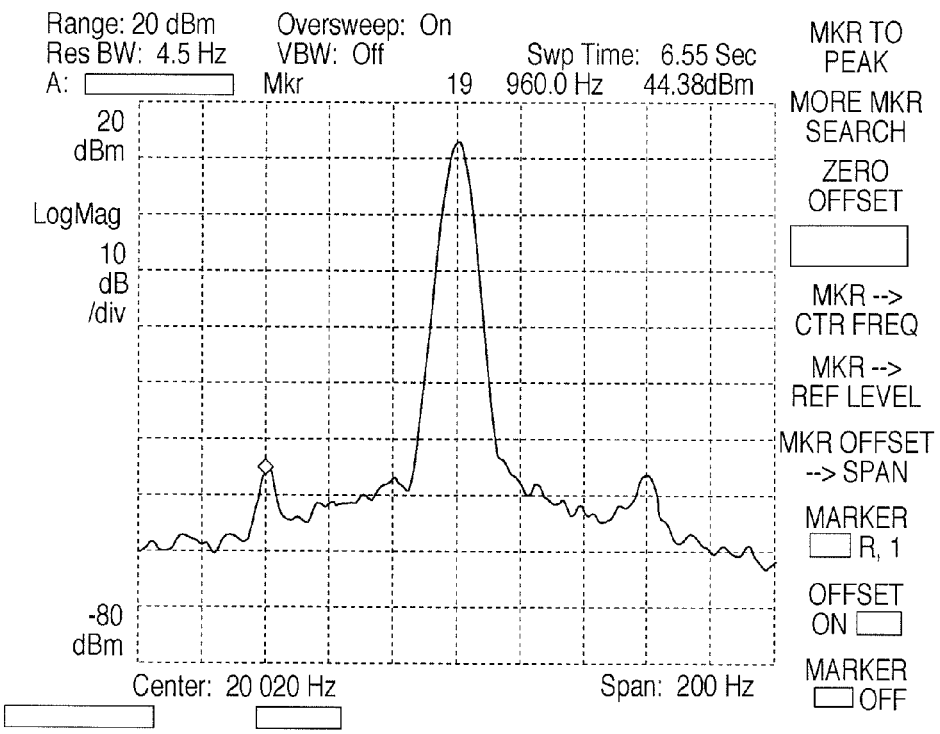

In FIG. 4, a 20 kHz carrier signal has been applied to the solenoid 112 by the carrier signal source 114, and the spectrum analyzer is adjusted to view the power spectrum centered on the carrier frequency. The sensor output has been connected to the spectrum analyzer through an inductor whose reactance cancels the capacitive reactance of the sensor (forming a series tuned circuit). Between the series inductor and the spectrum analyzer input, a shunt resistor to ground of the same value as the sensor resistance reduces the signal voltage by a factor of two. The carrier signal is seen as the large central peak, where the carrier level is shown at +13 dBm. This corresponds to an RMS voltage at 50Ω of about 1V or about 2.83V peak-to-peak relative to a sine wave. Also shown in FIG. 4 are two sidebands at +60 Hz and −60 Hz (the left and right peaks), which represent the up-converted signal of interest from baseband. The level of each sideband is about 3 dB to 4 dB lower than the 60 Hz baseband signal shown in FIG. 3. However, these two sidebands are coherent, and they can be synchronously demodulated (following a suitable amount of amplification), and their sum can be 6 dB stronger than each separate component. Thus, there is an effective conversion gain of 2 dB to 3 dB in this example. Not shown are the results of numerous tests for which sensors were inside a calibrated solenoid fed by a signal generator, in order to make absolute measurements of sensor output voltage versus magnetic flux density.

Another advantage with the sensor 100 is the reduction of sensor series capacitive reactance from about 100 MΩ and reduction of series resistance from several mega-Ohms relative to a 3 Hz baseband signal to about 25 kΩ reactance and about 2 kΩ resistance relative to a 20 kHz carrier and sidebands. The advantage is far greater considering that as shown above it is practical from about 20 kHz to at least about 40 kHz to apply a series inductance to cancel the reactance, leaving only the transducer resistance of about 2 kΩ. Table 1 shows possible impedance, reactance, and other values for a particular implementation of this sensor 100.

TABLE 1

| Freq | Z Mag | Z Phase | Resistive | Reactive | Resonant L (Henries) |
|---|---|---|---|---|---|
| 100 | 2.891M | −84.05 | 299686 | −2875425 | 4576.516 |
| 1000 | 338.6K | −82.17 | 46129 | −335443 | 53.389 |
| 2000 | 180.9K | −82.36 | 24051 | −179294 | 14.268 |
| 3000 | 125.12K | −82.49 | 16353 | −124047 | 6.581 |
| 4000 | 96.9K | −82.59 | 12497 | −96091 | 3.823 |
| 5000 | 79.24K | −82.67 | 10110 | −78592 | 2.502 |
| 6000 | 67.23K | −82.76 | 8473 | −66694 | 1.769 |
| 7000 | 58.44K | −82.83 | 7294 | −57983 | 1.318 |
| 8000 | 51.72K | −82.91 | 6384 | −51325 | 1.021 |
| 9000 | 46.52K | −83 | 5669 | −46173 | 0.817 |
| 10000 | 42.28K | −83.09 | 5087 | −41973 | 0.668 |
| 10000 | 42.86K | −83.34 | 4971 | −42571 | 0.678 |
| 15000 | 29.25K | −83.58 | 3271 | −29067 | 0.308 |
| 20000 | 22.08K | −83.69 | 2427 | −21946 | 0.175 |
| 30000 | 11.57K | −59.61 | 5853 | −9980 | 0.053 |
| 30400 | 15.57K | −44.95 | 11019 | −11000 | 0.058 |
| 32600 | 16.55K | −78.86 | 3198 | −16238 | 0.079 |
| 40000 | 12.8K | −84.94 | 1129 | −12750 | 0.051 |
| 50000 | 9.99K | −85.1 | 853 | −9953 | 0.032 |

As shown here, if the up-conversion process is applied at 40 kHz, the capacitive reactance is only about 13 k, where the inductance needed to cancel it is only about 50 mH (a practical value for this frequency) including parasitics. The resistive impedance left is only about 1 kΩ.

This means that much more low-frequency signal power can be obtained from the use of this internally-injected up-conversion type of sensor compared to sensors not having this modification. In particular embodiments, a 5 pT peak-to-peak signal may translate to about 85 nV or about 30 nV RMS. The available power from a 1 k impedance is about −151 dBm, and the amount of thermal noise in a 1 Hz bandwidth is about −174 dBm. At this frequency, a 1 dB noise figure is easily obtained. Therefore, with a bandwidth of 5 Hz, the SNR is about 15 dB with no event averaging, right out of the AFE. As a result, signal conditioning circuitry can be fabricated that does not substantially limit the ability to detect an excellent low frequency signal.

Note that the use of a sine wave-injected carrier is for illustration only. For example, in other embodiments, the sine current waveform can be replaced by a substantially or completely square waveform. With this type of waveform, the sensor 100 is either completely on or completely off for most of the time. Also, a square wave injection (as opposed to a sine wave injection) may increase the conversion gain and overall system sensitivity by 6 dB.

Further, in some embodiments, biasing the sensor's net magnetic field off with the electromagnet may be better than biasing the sensor's net magnetic field on. This is because the electromagnet's current may have noise associated with it, which would be irrelevant as the sensor is inactive at that time. During the other half-cycles, the electromagnet's current and its noise are shut off, while the inherently quiet permanent magnet(s) 108a-108b is/are the sole supplier of bias to sensitize the sensor 100.

Figure 5:
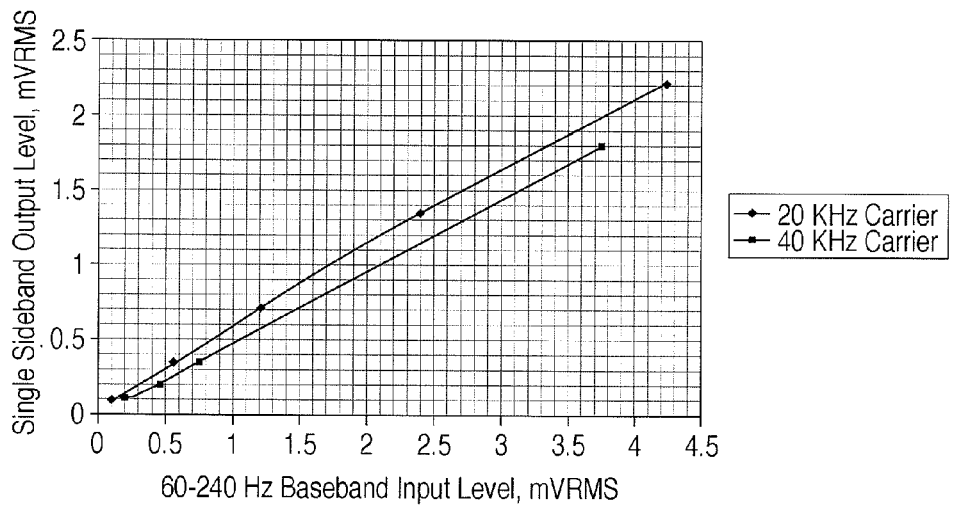

FIG. 5 illustrates heterodyning transfer characteristics of an example implementation of the sensor 100. This shows that the up-conversion process is substantially linear with respect to the output band versus the input band at both 20 kHz and 40 kHz. Single sideband loss could be about 6 dB, so double sideband loss would be about 0 dB. Note that it has been shown that this up-conversion process can be substantially linear both in amplitude and in phase (time delay constant with frequency).

In another aspect of this disclosure, the sensor 100 of FIG. 1 can operate at resonance. At a certain frequency, the propagation time across the dimension of the piezo-electric material equals 0.5 wavelength. At this frequency, a resonance effect causes the piezo-electric material to produce a significantly higher output voltage (such as at least 20 times more) per unit strain. Such large transducer gain can make front-end noise negligible, such as down to fields of 10 pT. The ability to shift (up-convert or down-convert) from any frequency to the resonance frequency permits one to take advantage of this resonance effect, regardless of the frequency of magnetic fields being measured. In particular embodiments of the sensor 100, the resonance frequency may be about 32 kHz, although the exact resonance frequency varies depending on the structure of the sensor.

Figure 6:
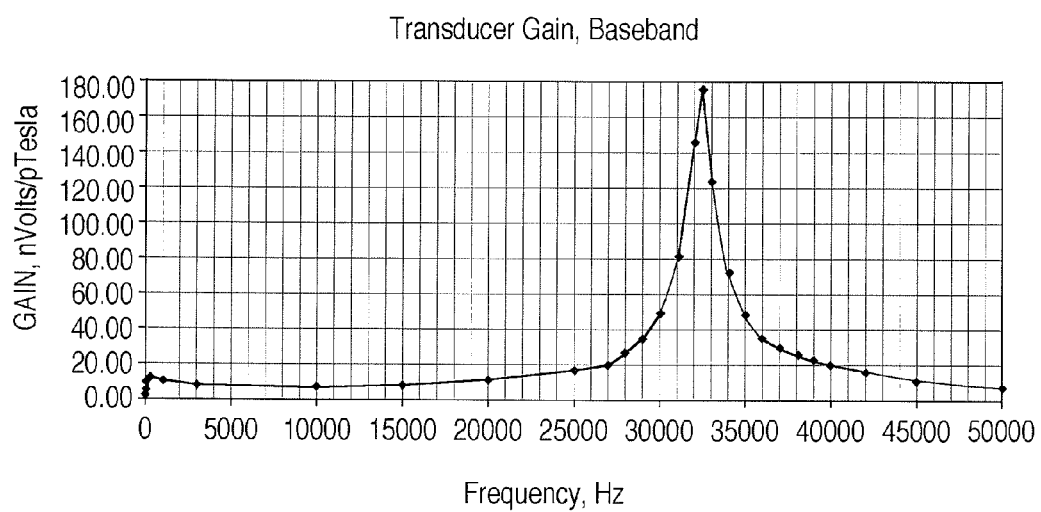

FIG. 6 illustrates transducer gain of an example sensor 100 as a function of frequency for a particular implementation of the sensor 100. As shown in FIG. 6, except for frequencies within influence of the resonance point, the transducer gain appears to be within the range from about 6 nV/pT to about 11 nV/pT. However, the gain at the resonance frequency, 32.4 kHz in this example, is significantly larger at close to 180 nV/pT. Other sensors (such as those having a larger number of piezo-electric and magneto-strictive layers and a plastic enclosure with plastic end caps and an aluminum foil lining) could have even higher transducer gain at resonance, such as close to 500 nV/pT.

Note that while up-conversion (including to the sensor's resonance frequency) is discussed above, down-conversion in general and down-conversion to the sensor's resonance frequency in particular can also be performed. For example, there may be some situations in which it is desired to measure the strength of a magnetic field whose frequency is above the sensor's resonance frequency. By down-converting to the sensor's resonance frequency, the SNR of the sensor could again be improved.

It has been surmised that almost all or at least a significant portion of the noise in this sensor structure comes from the piezo-electric material, rather than from the magneto-strictive material. It has been shown that the sensor as a whole is much quieter at higher frequencies than at lower frequencies. Such knowledge forms part of the basis for expecting to achieve better sensitivity through the use of the frequency up-conversion or down-conversion process and is in addition to the impedance advantage discussed above. Inasmuch as a frequency up-conversion or down-conversion process occurs before a signal reaches the piezo-electric material, the signal can already be at a frequency where the piezo-electric material is quieter when the signal reaches the piezo-electric layer(s). It has been shown that the SNR at the sensor's resonance is approximately 10 dB higher than when the sensor is not in resonance. In addition to making the sensor more sensitive at resonance, this fact supports the supposition that most or all of the noise comes from the piezo-electric material.

The sensor 100 shown in FIG. 1 can be used in a wide variety of applications. For example, the sensor 100 could be used to measure weak magnetic fields associated with currents in a patient's heart. This is described more fully in the U.S. provisional patent applications incorporated by reference above. The sensor 100 could also be used for sensing or measuring very small currents in electronic circuits. The sensor 100 could further be used in any other application requiring the detection or measurement of extremely weak magnetic fields or currents at a distance.

The sensor 100 has been described above as using one or more permanent magnets and one or more electromagnets to create a time-varying biasing magnetic field within the sensor 100. However, other techniques could be used to generate the time-varying biasing field. For example, one or more permanent magnets that move within or outside of the sensor 100 could be used to generate a time-varying magnetic field within the sensor 100, and the electromagnet could be omitted. As a particular example, one or more permanent magnets could be moved with back and forth translation so that the sensor would vary from strongly on to almost or completely off. As another particular example, one or more permanent magnets could be rotated to yield a balanced modulator type of response. As yet another particular example, one or more fixed permanent magnets could be used with one or more movable permanent magnets (such as rotatable magnets) to generate a total biasing field that has a raised cosine shape. Another way to generate a time-varying biasing magnetic field is to use one or more electromagnets that are controlled as described above (such as with a sine or square wave) without any permanent magnets. In each of these embodiments, as with the use of both permanent magnet(s) and electromagnet(s), the frequency up-conversion or down-conversion is occurring within the sensor itself.

In other embodiments, the frequency up-conversion or down-conversion could be achieved by chopping the surrounding magnetic field that is being measured by the sensor or otherwise performing the up- or down-conversion prior to the sensor. For example, the sensor could be moved (such as rotated or translated) relative to the magnetic field being measured. As another example, the sensor could be intermittently shielded from the surrounding magnetic field to be measured. This could be accomplished by using a shutter, such as a slotted disc, made from a magnetic shielding material like Mu metal. The slotted disc could spin in order to alternatively transmit and block the low-frequency magnetic field being measured. The sensor could also be encased in a magnetic shielding material so that the surrounding magnetic field only reaches the sensor through the slotted disc. In these embodiments, the sensor 100 may or may not include a time-varying biasing magnetic field, such as one produced using an electromagnet.

In still other embodiments, one or more electromagnets without permanent magnets could be used to repeatedly reverse the polarity of the sensor's output. The electromagnet's drive current in this case could have no DC component. This causes the sensor to act as a balanced modulator with a small output at the carrier frequency. For the embodiment of the sensor used with respect to FIG. 2 above, this could be achieved by applying to the solenoid 112 a sine or square wave symmetric around 0 A and having a peak-to-peak range of about 1.2 A.

In general, all of these embodiments are characterized by the fact that the up-conversion or down-conversion is performed before the surrounding magnetic field is converted into an electrical signal within the sensor. The up-conversion or down-conversion could involve the use of a time-varying biasing magnetic field, a time-invariant biasing magnetic field, a chopped magnetic field to be measured, or any suitable combination thereof. As long as the up-conversion or down-conversion is performed before the surrounding magnetic field is converted into an electrical signal, at least some of the benefits previously discussed remain, regardless of the mechanism by which the up-conversion or down-conversion is achieved.

Although FIG. 1 illustrates one example of a magneto-electric sensor 100 with injected up-conversion or down-conversion, various changes may be made to FIG. 1. For example, the sensor 100 could include any number of magneto-strictive and piezo-electric layers. The sensor 100 could also include any number of permanent magnets, electromagnets, and other components in any suitable configuration. As a particular example, the electromagnet's windings within the sensor could be arranged so that, with the correct drive current amplitude and/or phasing, the frequency conversion carrier signal seen at the sensor output along with the information-carrying sidebands could be reduced in level. The sensor 100 could further include any suitable electromagnet(s) for reducing or cancelling the biasing magnetic field from the permanent magnet(s). Although FIGS. 2 through 6 illustrate additional details of example embodiments of the sensor 100, these details are for illustration only. Embodiments of the sensor 100 could operate in ways other than as shown in FIGS. 2 through 6.

Figure 7:
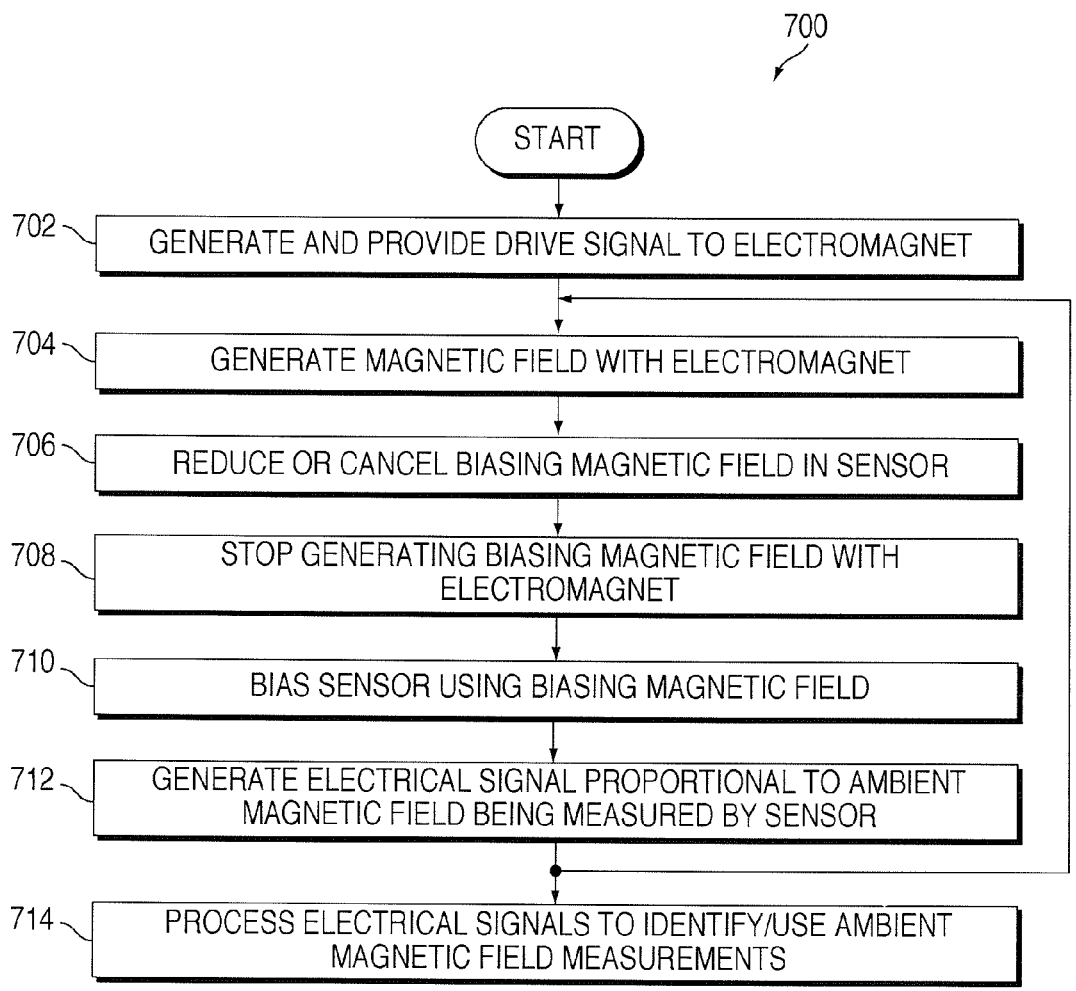
FIG. 7 illustrates an example method for measuring a magnetic field using a magneto-electric sensor with injected up-conversion or down-conversion according to this disclosure.

FIG. 7 illustrates an example method 700 for measuring a magnetic field using a magneto-electric sensor with injected up-conversion or down-conversion according to this disclosure. As shown in FIG. 7, a drive signal is generated and provided to an electromagnet in a magneto-electric sensor at step 702. This could include, for example, the carrier signal source 114 generating a current having a square waveform ranging between 0 A and a maximum value, where the current transitions up and down at a specified carrier frequency and is provided to the solenoid 112. Of course, any other suitable drive signal could be generated.

The electromagnet generates a magnetic field at step 704, and the magnetic field reduces or cancels a biasing magnetic field in the sensor at step 706. This could include, for example, the solenoid 112 generating the magnetic field based on the current flowing through the solenoid 112 from the carrier signal source 114, where the current has the maximum value (if a square wave is being used). The magnetic field generated by the solenoid 112 can reduce or cancel the biasing magnetic field generated by the permanent magnet(s) 108a-108b in the sensor 100. During this time, the sensor 100 is desensitized and is not used to capture measurements of a surrounding magnetic field.

The electromagnet stops generating the magnetic field at step 708, and the sensor is biased with the biasing magnetic field at step 710. This could include, for example, the solenoid 112 stopping the generation of the magnetic field because the current from the carrier signal source 114 has dropped to zero. The magnetic field generated by the permanent magnet(s) 108a-108b sensitizes the magneto-strictive layers 104a-104b in the sensor 100. As a result, the sensor generates an electrical signal proportional to the surrounding magnetic field being measured by the sensor at step 712.

At this point, another cycle may repeat where the sensor 100 is desensitized by the electromagnet and then sensitized for another measurement. The electrical signals can also be processed at any suitable time at step 714, such as in parallel with or after steps 704-712. The processing can involve analyzing the electrical signals output by the sensor 100 to identify the sidebands of the carrier frequency. As discussed above, the up-conversion or down-conversion performed within or before the sensor 100 causes a targeted signal to leave the sensor 100 as coherent sidebands near the carrier frequency. These sidebands can be identified, processed, and combined to obtain a measurement of the ambient magnetic field. The measurement can then be used in any suitable manner.

Although FIG. 7 illustrates one example of a method 700 for measuring a magnetic field using a magneto-electric sensor with injected up-conversion or down-conversion, various changes may be made to FIG. 7. For example, various steps in FIG. 7 could overlap, occur in parallel, occur serially, occur in a different order, or occur any number of times. Also, as described above, other techniques could be used to obtain the up-conversion or down-conversion, including using electromagnet(s) without permanent magnet(s), moving permanent magnet(s), moving the sensor, or intermittently shielding the sensor from the surrounding magnetic field.

It may be advantageous to set forth definitions of certain words and phrases that have been used within this patent document. The term "couple" and its derivatives refer to any direct or indirect communication between two or more components, whether or not those components are in physical contact with one another. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A sensor apparatus for sensing magnetic signals with a sensed signal frequency range, comprising:
   a sensor stack comprising alternating layers of at least two layers of magneto-strictive material and at least one layer of piezo-electric material, configured with the at least one piezo-electric layer between, and physically attached to, the at least two magneto-strictive layers; and
   a biasing arrangement configured to apply to the magneto-strictive layers a time-varying biasing magnetic field, the biasing magnetic field including a substantially constant (DC) bias component and a time-varying bias component with a carrier signal frequency;
   such that magneto-strictive layers exhibit a magneto-strictive response to a heterodyned magnetic signal corresponding to heterodyning the time-varying biasing magnetic field and the sensed magnetic signal; and
   wherein the piezo-electric layer is responsive to the magneto-strictive response to the heterodyned magnetic signal to generate electrical signals corresponding to the heterodyned magnetic signal at the heterodyned frequency.

2. The sensor apparatus of claim 1, wherein the biasing arrangement comprises:
   a DC bias arrangement configured to apply to the magneto-strictive layers a substantially constant (DC) biasing magnetic field; and
   a carrier signal arrangement configured to apply to the magneto-strictive layers a time-varying carrier biasing magnetic field with the carrier signal frequency;
   such that the magneto-restrictive layers are biased with the biasing magnetic field including the substantially constant bias (DC) component from the DC bias arrangement, and the time-varying bias component from the carrier signal arrangement.

3. The sensor apparatus of claim 2,
   wherein the DC bias arrangement comprises at least one permanent magnet near at least one magneto-strictive layer; and wherein the carrier signal arrangement comprises a solenoid with windings around the sensor stack.

4. The sensor apparatus of claim 1, wherein the carrier signal frequency is selected to up-convert the sensed magnetic signal to a heterodyned frequency range corresponding to a frequency range in which the piezo-electric material exhibits at least one of:
 substantially lower reactance than the sensed magnetic signal frequency range, and substantially lower noise than the sensed magnetic signal frequency range.

5. The sensor apparatus of claim 1, wherein the carrier signal frequency is selected to frequency-convert the sensed magnetic signal to a heterodyned frequency range corresponding to a resonant frequency of the piezo-electric material.

6. A sensor system for sensing magnetic signals with a sensed signal frequency range, comprising:
 a sensor stack comprising alternating layers of at least two layers of magneto-strictive material and at least one layer of piezo-electric material, configured with the at least one piezo-electric layer between, and physically attached to, the at least two magneto-strictive layers; and
 a biasing arrangement configured to apply to the magneto-strictive layers a time-varying biasing magnetic field, the biasing magnetic field including a substantially constant (DC) bias component and a time-varying bias component with a carrier signal frequency;
 such that magneto-strictive layers exhibit a magneto-strictive response to a heterodyned magnetic signal corresponding to heterodyning the time-varying biasing magnetic field and the sensed magnetic signal; and
 wherein the piezo-electric layer is responsive to the magneto-strictive response to the heterodyned magnetic signal to generate electric signals corresponding to the heterodyned magnetic signal at the heterodyne frequency; and
 signal extraction circuitry configured to extract from electric signals generated by the piezo-electric layer in response to the magneto-strictive response, a sensor output signal corresponding to the sensed magnetic signal.

7. The sensor system of claim 6, wherein the biasing arrangement comprises:
 a DC bias arrangement configured to apply to the magneto-strictive layers a substantially constant (DC) biasing magnetic field; and
 a carrier signal arrangement configured to apply to the magneto-strictive layers a time-varying carrier biasing magnetic field with the carrier signal frequency;
 such that the magneto-restrictive layers are biased with the biasing magnetic field including the substantially constant bias (DC) component from the DC bias arrangement, and the time-varying bias component from the carrier signal arrangement.

8. The sensor system of claim 7,
 wherein the DC bias arrangement comprises at least one permanent magnet near at least one magneto-strictive layer; and
 wherein the carrier signal arrangement comprises a solenoid with windings around the sensor stack.

9. The sensor system of claim 6, wherein the carrier signal frequency is selected to up-convert the sensed magnetic signal to a heterodyned frequency range corresponding to a frequency range in which the piezo-electric material exhibits at least one of:
 substantially lower reactance than the sensed magnetic signal frequency range, and substantially lower noise than the sensed magnetic signal frequency range.

10. The sensor system of claim 6, wherein the carrier signal frequency is selected to frequency-convert the sensed magnetic signal to a heterodyned frequency range corresponding to a resonant frequency of the piezo-electric material.

11. A method of sensing magnetic signals with a sensed signal frequency range, using a sensor stack including alternating layers of at least two layers of magneto-strictive material and at least one layer of piezo-electric material, configured with the at least one piezo-electric layer between, and physically attached to, the at least two magneto-strictive layers, comprising:
 biasing the magneto-strictive layers with a time-varying biasing magnetic field, the biasing magnetic field including a substantially constant (DC) bias component and a time-varying bias component with a carrier signal frequency;
 sensing the magnetic signals such that
  the magneto-strictive layers exhibit a magneto-strictive response to a heterodyned magnetic signal corresponding to heterodyning the time-varying biasing magnetic field and the sensed magnetic signal; and
  the piezo-electric layer is responsive to the magneto-strictive response to the heterodyned magnetic signal to generate electrical signals corresponding to the heterodyned magnetic signal at the heterodyne frequency.

12. The method of claim 11, wherein biasing the magneto-strictive layers comprises:
 applying to the magneto-strictive layers a substantially constant (DC) biasing magnetic field; and
 applying to the magneto-strictive layers a time-varying carrier biasing magnetic field with the carrier signal frequency;
 such that the magneto-restrictive layers are biased with the biasing magnetic field including the substantially constant bias (DC) component from the DC bias arrangement, and the time-varying bias component from the carrier signal arrangement.

13. The method of claim 12,
 wherein the substantially constant (DC) biasing magnetic field is provided by at least one permanent magnet near at least one magneto-strictive layer; and
 wherein the time-varying carrier biasing magnetic field is provided by a solenoid with windings around the sensor stack.

14. The method of claim 11, wherein the carrier signal frequency is selected to up-convert the sensed magnetic signal to a heterodyned frequency range corresponding to a frequency range in which the piezo-electric material exhibits at least one of:
 substantially lower reactance than the sensed magnetic signal frequency range, and substantially lower noise than the sensed magnetic signal frequency range.

15. The method of claim 11, wherein the carrier signal frequency is selected to frequency-convert the sensed magnetic signal to a heterodyned frequency range corresponding to a resonant frequency of the piezo-electric material.

* * * * *